US010322527B2

(12) United States Patent
Manabe et al.

(10) Patent No.: US 10,322,527 B2
(45) Date of Patent: Jun. 18, 2019

(54) KNEADER INTERNAL INSPECTION DEVICE

(71) Applicant: Kobe Steel, Ltd., Hyogo (JP)

(72) Inventors: Chitaka Manabe, Kobe (JP); Eiji Takahashi, Kobe (JP); Toshihide Fukui, Kobe (JP); Hodaka Miura, Takasago (JP)

(73) Assignee: Kobe Steel, Ltd., Hyogo (JP)

( * ) Notice: Subject to any disclaimer, the term of this patent is extended or adjusted under 35 U.S.C. 154(b) by 228 days.

(21) Appl. No.: 15/328,807

(22) PCT Filed: Jun. 12, 2015

(86) PCT No.: PCT/JP2015/066968
§ 371 (c)(1),
(2) Date: Jan. 24, 2017

(87) PCT Pub. No.: WO2016/024435
PCT Pub. Date: Feb. 18, 2016

(65) Prior Publication Data
US 2017/0225359 A1 Aug. 10, 2017

(30) Foreign Application Priority Data
Aug. 11, 2014 (JP) .................. 2014-163711

(51) Int. Cl.
*H04N 7/18* (2006.01)
*B29B 7/28* (2006.01)
(Continued)

(52) U.S. Cl.
CPC ................. *B29B 7/28* (2013.01); *B01F 7/04* (2013.01); *B01F 15/00259* (2013.01);
(Continued)

(58) Field of Classification Search
CPC .......... B29B 7/183; B29B 7/28; B29B 7/186; B29B 7/7495; B29B 7/82; B29B 7/22;
(Continued)

(56) References Cited

U.S. PATENT DOCUMENTS 5,672,006 A 9/1997 Hanada et al.
2013/0192353 A1 8/2013 Hatcher
(Continued)

FOREIGN PATENT DOCUMENTS

CN 202284708 U 6/2012
CN 104081190 A 10/2014
(Continued)

OTHER PUBLICATIONS

"Scissor Lift Robot with 360 Pan/Tilt Camera System", YouTube, URL: https://www.youtube.com/watch?v=4zGy_jjgeno; Pub. May 13, 2013 (Year: 2013).*
(Continued)

*Primary Examiner* — Sathyanaraya V Perungavoor
*Assistant Examiner* — Peet Dhillon
(74) *Attorney, Agent, or Firm* — Studebaker & Brackett PC

(57) ABSTRACT

A kneader internal inspection device according to the present invention suspends and supports a photographing unit, which is arranged in an interior of a kneader and which photographs the interior, so as to be vertically movable in the interior of the kneader. Therefore, such a kneader internal inspection device is capable of easily inspecting the interior of the kneader.

8 Claims, 13 Drawing Sheets

(51) Int. Cl.

| | | |
|---|---|---|
| *B01F 7/04* | (2006.01) | |
| *B29B 7/22* | (2006.01) | |
| *G01N 21/954* | (2006.01) | |
| *B29B 7/18* | (2006.01) | |
| *B01F 15/00* | (2006.01) | |
| *B01F 15/06* | (2006.01) | |
| *B29B 7/82* | (2006.01) | |
| *G03B 17/56* | (2006.01) | |
| *H04N 5/225* | (2006.01) | |
| *H04N 5/232* | (2006.01) | |
| *B29B 7/26* | (2006.01) | |
| *G01N 21/84* | (2006.01) | |
| *B29B 7/74* | (2006.01) | |

(52) U.S. Cl.
CPC ............ *B01F 15/066* (2013.01); *B29B 7/183* (2013.01); *B29B 7/22* (2013.01); *B29B 7/266* (2013.01); *B29B 7/82* (2013.01); *G01N 21/954* (2013.01); *G03B 17/561* (2013.01); *H04N 5/2256* (2013.01); *H04N 5/23203* (2013.01); *H04N 5/23296* (2013.01); *H04N 7/185* (2013.01); *B01F 2015/061* (2013.01); *B01F 2215/0049* (2013.01); *B29B 7/186* (2013.01); *B29B 7/7495* (2013.01); *G01N 21/84* (2013.01)

(58) Field of Classification Search
CPC .... G01N 21/954; G01N 21/84; G03B 17/561; H04N 5/2256; H04N 5/23203; H04N 5/23296; H04N 7/185; B01F 7/04; B01F 15/066; B01F 15/00259; B01F 2015/061; B01F 2215/0049; A21C 1/06
USPC .......................................................... 348/82
See application file for complete search history.

(56) References Cited

U.S. PATENT DOCUMENTS

| | | | |
|---|---|---|---|
| 2013/0194412 A1 | 8/2013 | Hatcher et al. | |
| 2013/0194413 A1 | 8/2013 | Hatcher et al. | |
| 2013/0314529 A1 | 11/2013 | Hoffman | |
| 2013/0335530 A1 | 12/2013 | Hatcher, Jr. et al. | |
| 2013/0335549 A1 | 12/2013 | Hatcher, Jr. et al. | |
| 2014/0055596 A1 | 2/2014 | Hatcher, Jr. et al. | |
| 2015/0054939 A1 | 2/2015 | Deascanis et al. | |
| 2015/0264202 A1* | 9/2015 | Pawlowski | H04N 1/00106 348/207.11 |
| 2015/0300920 A1 | 10/2015 | Deascanis et al. | |
| 2015/0338353 A1 | 11/2015 | Bancalari et al. | |
| 2016/0330351 A1 | 11/2016 | Deascanis et al. | |

FOREIGN PATENT DOCUMENTS

| | | | | |
|---|---|---|---|---|
| JP | S62-025242 A | 2/1987 | | |
| JP | S62-280642 A | 12/1987 | | |
| JP | H02-059650 A | 2/1990 | | |
| JP | H0259650 A | * 12/1990 | ............... | H03H 9/50 |
| JP | H08-230020 A | 9/1996 | | |
| JP | H09-329554 A | 12/1997 | | |
| JP | H11-108821 A | 4/1999 | | |
| JP | 2000-230231 A | 8/2000 | | |
| JP | 3095656 B2 | 10/2000 | | |
| JP | 2004230874 A | * 8/2004 | | |
| JP | 2005-104076 A | 4/2005 | | |
| JP | 2005-214599 A | 8/2005 | | |
| JP | 3756766 B2 | 3/2006 | | |
| JP | 2011-196019 A | 10/2011 | | |
| KR | 20-0200303 Y1 | 10/2000 | | |
| KR | 10-2008-0029432 A | 4/2008 | | |

OTHER PUBLICATIONS

Notification of Transmittal of Translation of the International Preliminary Report on Patentability and English translation of the Written Opinion of the International Searching Authority; PCT/JP2015/066968 dated Feb. 23, 2017; 10pp.

International Search Report issued in PCT/JP2015/066968; dated Aug. 25, 2015.

* cited by examiner

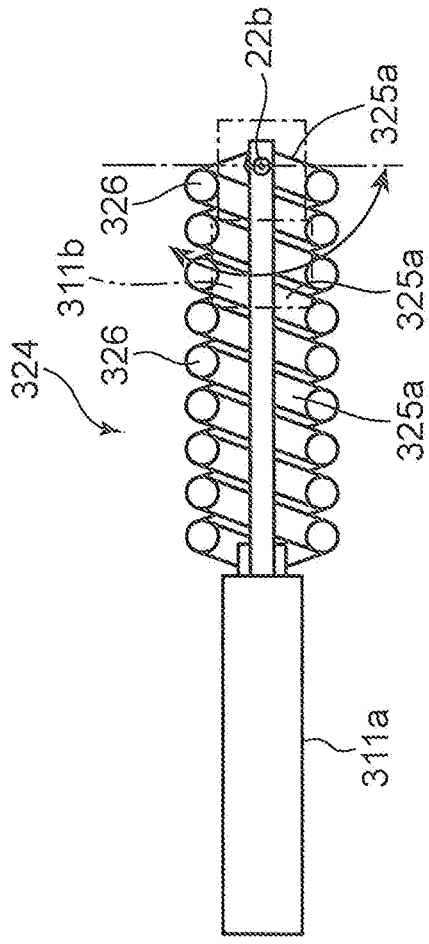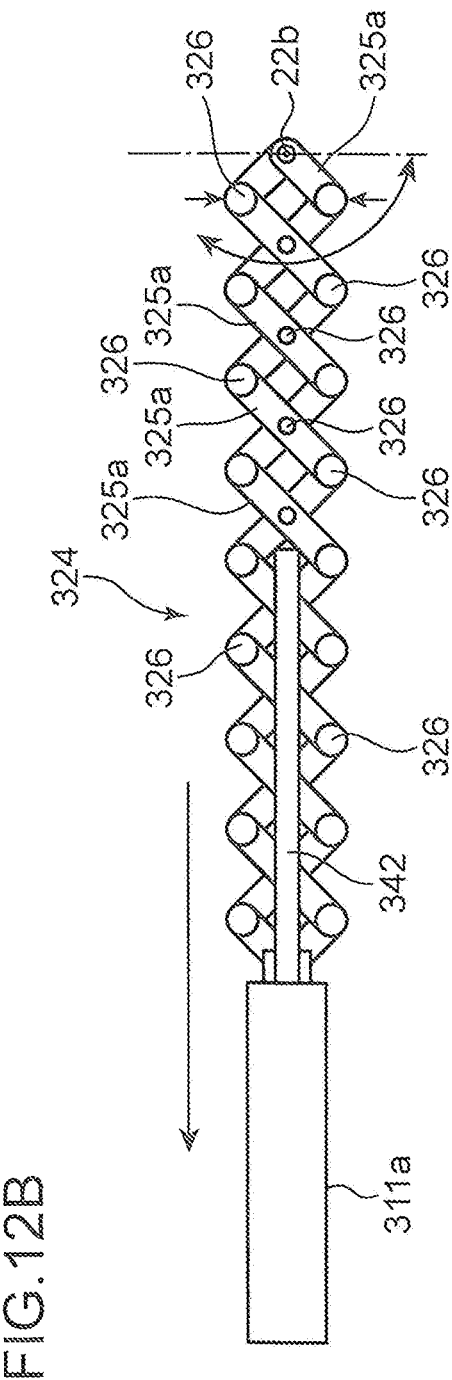
FIG.12A
FIG.12B

KNEADER INTERNAL INSPECTION DEVICE

TECHNICAL FIELD

The present invention relates to a kneader internal inspection device for inspecting an interior of a kneader which kneads rubber, resin, or the like.

BACKGROUND ART

Kneaders which knead rubber, resin, or the like are conventionally known. For example, Patent Literature 1 discloses an example of a kneader. The kneader disclosed in Patent Literature 1 includes a rotor rotatably arranged in an interior of a chamber formed by a casing and kneads a processed article such as rubber or resin by deforming the processed article so as to tear the processed article apart with a rotation of the rotor.

Since such a kneader is used in a state where large friction is created between the processed article and the rotor as well as an inner surface of the casing, the kneader must withstand abrasion. In particular, when a substance with high hardness such as silica is incorporated into raw material rubber of tires as of late, abrasion becomes more severe. For this reason, constituent members of a kneader are often subjected to chromium plating, spray coating, and the like to impart abrasion resistance.

However, abrasion proceeds during a period of use and a surface treatment layer may become thinner or may peel off. In addition, since contents of operation (hardness of processed raw materials and the like) even differ among machines of a same model, it is difficult to determine a state of wear and tear simply based on operation time. Therefore, when performing equipment maintenance, it is important that such states are inspected.

Conventionally, such inspections involve, for example, opening a door (drop door) provided on a kneader and have an experienced worker visually and manually inspect locations corresponding to check points. Therefore, when including personnel for ensuring safety and time required for machine shutdown and startup, inspections are labor-intensive and time-consuming. In addition, whether or not an inspection is performed is determined based on history and past results of maintenance and an operation status of a machine. If a determination of whether or not such a full-scale inspection is immediately necessary can be made with a simple inspection, an appropriate maintenance plan can be formulated and a reduction in cost can be achieved. Significant advantages may be particularly gained if reduction can be achieved in work associated with inspection and downtime of the machine.

However, since kneaders are structured such that a rotor rotates inside a space called a chamber as described in, for example, Patent Literature 1, an entirety of an interior is not viewable in one glance and an inspection of the interior requires changing viewing directions. Therefore, work accompanying an inspection is difficult.

In addition, for example, according to Patent Literature 2, a casing forming a chamber has a two-piece structure which can be vertically divided. During an inspection, the casing is separated and opened to enable inspection of an interior thereof.

However, according to Patent Literature 2, opening and dividing the casing into two pieces is labor-intensive and time-consuming, and restoration such as assembly of the casing after an inspection is similarly labor-intensive and time-consuming. Therefore, an inspection cannot be readily performed.

Since kneaders are machines subjected to extremely large forces during kneading, such a two-piece structure is unfavorable in terms of strength and requires reinforcement such as increasing wall thickness in order to ensure that strength is comparable to that of an integrated structure which cannot be divided into two pieces. Therefore, such a two-piece structure is also unfavorable in terms of weight and size.

CITATION LIST

Patent Literature

Patent Literature 1: Japanese Patent No. 3095656
Patent Literature 2: Japanese Patent No. 3756766

SUMMARY OF INVENTION

The present invention has been made in consideration of the circumstances described above, and an object thereof is to provide a kneader internal inspection device capable of easily inspecting an interior of a kneader.

A kneader internal inspection device according to the present invention suspends and supports a photographing unit which is arranged in an interior of a kneader and which photographs the interior so as to be vertically movable in the interior of the kneader. Therefore, such a kneader internal inspection device is capable of easily inspecting the interior of the kneader.

The above and other objects, features, and advantages of the present invention will become apparent by reference to the following detailed description when considered together with the accompanying drawings.

BRIEF DESCRIPTION OF DRAWINGS

FIG. 12 is a diagram showing yet another embodiment of the camera holding member of the photographing unit used in the kneader internal inspection device shown in FIG. 1.

DESCRIPTION OF EMBODIMENTS

Figure 1:
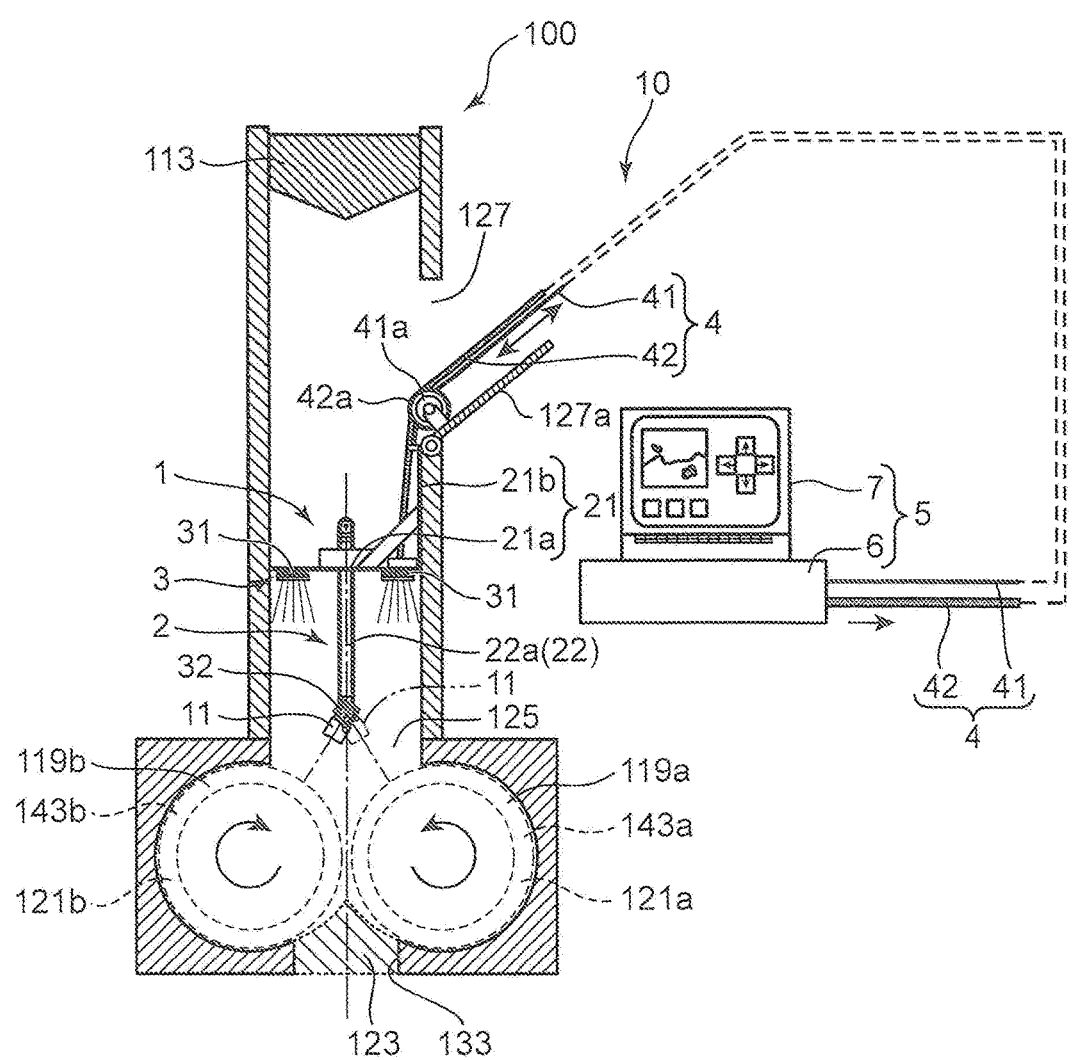
FIG. 1 is a schematic diagram of a state where an interior of a kneader is being inspected by a kneader internal inspection device according to an embodiment.

Hereinafter, embodiments of the present invention will be described with reference to the drawings. It should be noted that components assigned same reference numerals in the respective drawings represent same components and descriptions thereof will be omitted as appropriate. In the present description, components will be denoted by a reference numeral without a suffix when collectively referred to while an individual component will be denoted by a reference numeral with a suffix.

A kneader internal inspection device 10 according to the present embodiment is a device used to inspect an interior of a kneader 100. Before describing the kneader internal inspection device 10 according to the present embodiment, the kneader 100 on which the kneader internal inspection device 10 is used will be described.

Figure 5:
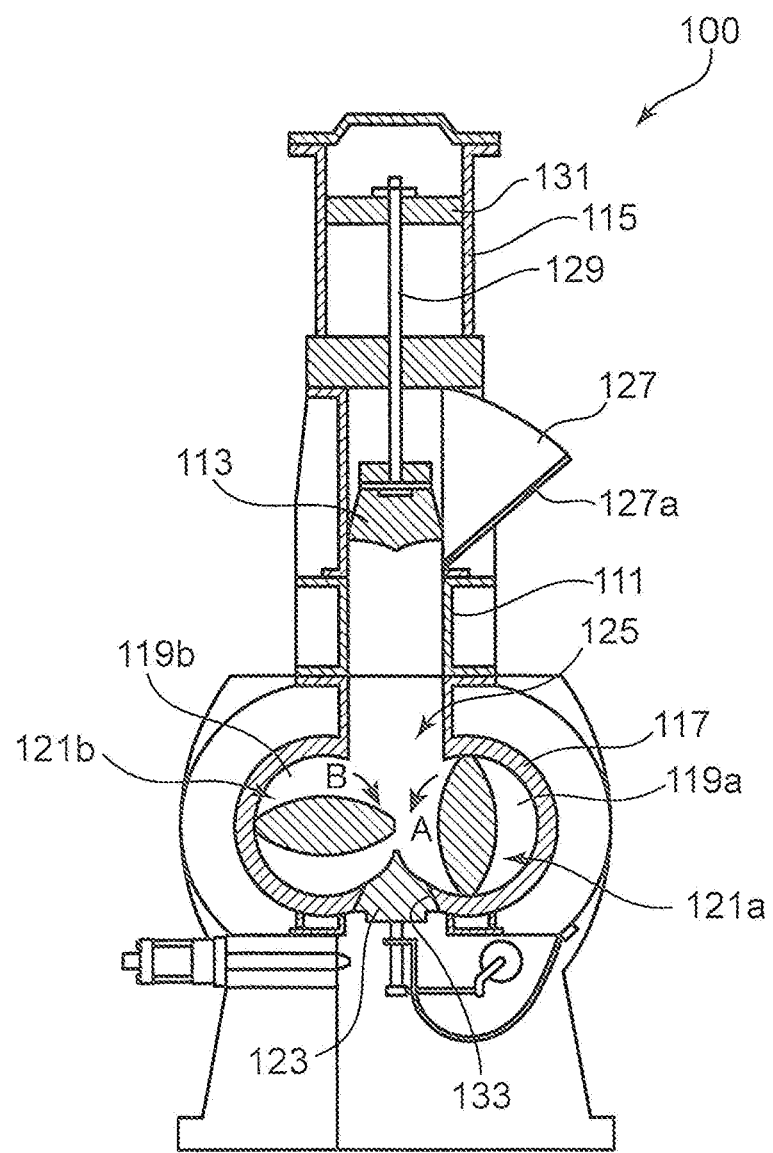
FIG. 5 is a sectional view of a kneader on which the kneader internal inspection device shown in FIG. 1 is used.
Figure 6:
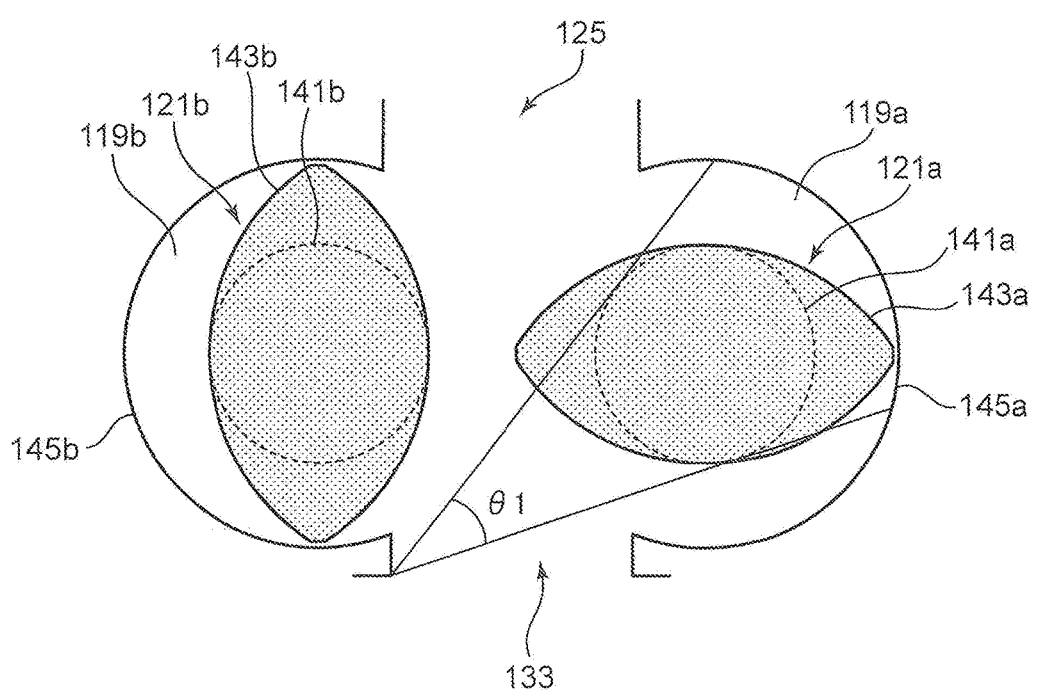
FIG. 6 is a sectional view of a rotor of the kneader shown in FIG. 5.
Figure 7:
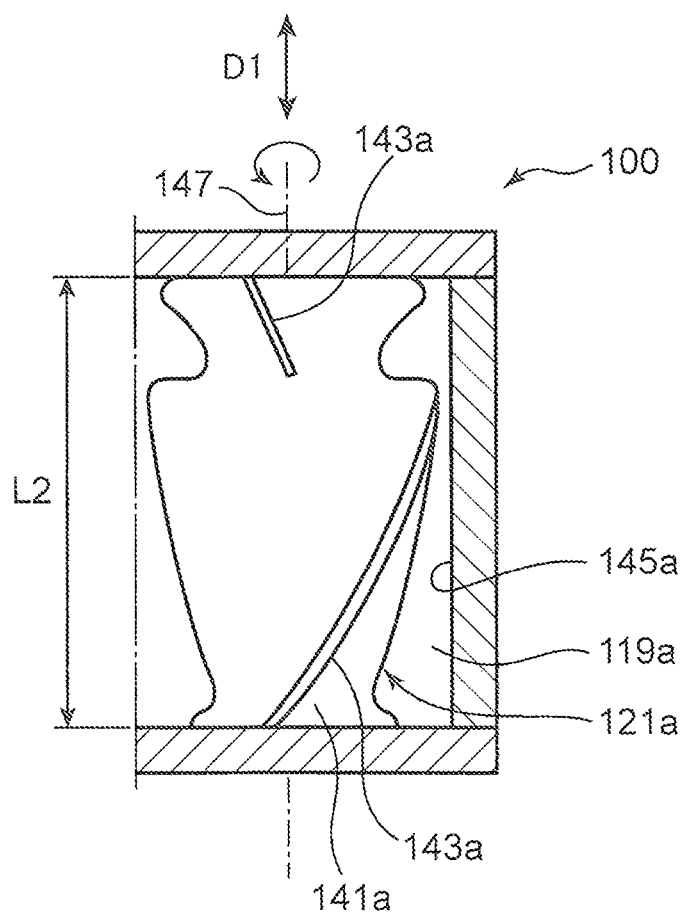
FIG. 7 is a plan view having a part of a kneading chamber of the kneader shown in FIG. 5 as a section.

FIG. 5 is a sectional view of a kneader on which the kneader internal inspection device shown in FIG. 1 is used. FIG. 6 is a sectional view of a rotor of the kneader shown in FIG. 5. FIG. 7 is a plan view having a part of a kneading chamber of the kneader shown in FIG. 5 as a section. The kneader 100 used in the present embodiment is, for example, a biaxial batch mixer as shown in FIG. 5 to FIG. 7 which creates a kneaded article by kneading, for example, a rubber raw material and various materials (a reinforcing agent, a plasticizer, an age inhibitor, and the like). While an example of the kneader 100 which creates a kneaded article to become a rubber product is described in the present embodiment, the kneader internal inspection device 10 according to the present embodiment is not limited thereto and can also be applied to a kneader which creates a kneaded article to become a plastic product.

As shown in FIG. 5, the kneader 100 includes a material feed throat 111, a floating weight 113, a pneumatic cylinder 115, a casing 117, first and second kneading chambers 119a and 119b, two rotors 121a and 121b, and a drop door 123.

More specifically, the material feed throat 111 extends vertically above the casing 117. The pneumatic cylinder 115 is provided at an upper end of the material feed throat 111. A piston rod 129 is arranged from an interior of the pneumatic cylinder 115 to an interior of the material feed throat 111. A piston 131 fixed to an upper end of the piston rod 129 is arranged in the interior of the pneumatic cylinder 115.

The floating weight 113 is arranged in the interior of the material feed throat 111. The floating weight 113 is fixed to a lower end of the piston rod 129 and moves vertically together with the piston rod 129.

A lower end of the material feed throat 111 is communicated with the two kneading chambers 119a and 119b through a material supply port 125 formed on the casing 117.

A hopper 127 is provided on a side surface of the material feed throat 111. Materials (the rubber raw material and the various materials) are fed into the material feed throat 111 from the hopper 127. In addition, the hopper 127 is provided with a hopper openable lid 127a.

When the floating weight 113 descends due to an action of the pneumatic cylinder 115, the materials fed into the material feed throat 111 are supplied to the first kneading chamber 119a and the second kneading chamber 119b.

The first kneading chamber 119a and the second kneading chamber 119b are formed in an interior of the casing 117. The first kneading chamber 119a and the second kneading chamber 119b respectively have an approximately cylindrical shape that extends in a perpendicular direction relative to a paper surface of FIG. 6.

A first rotor 121a is arranged inside the first kneading chamber 119a, and a second rotor 121b is arranged inside the second kneading chamber 119b. The rotors 121a and 121b extend in a perpendicular direction relative to a paper surface of FIG. 5 and, as power is imparted thereto from a motor (not shown), the first rotor 121a rotates in a direction of an arrow A (for example, counterclockwise) and the second rotor 121b rotates in a direction of arrow B (for example, clockwise) which is opposite to the direction of the arrow A.

A kneaded article discharge port 133 for discharging a kneaded article is provided in a lower part of the casing 117.

The drop door 123 functions as a lid which blocks the kneaded article discharge port 133. The drop door 123 is arranged so as to be vertically movable. The kneaded article discharge port 133 opens as the drop door 123 descends. The kneaded article discharge port 133 closes as the drop door 123 ascends.

FIG. 6 and FIG. 7 are, respectively, enlarged views of the kneading chambers 119a and 119b and the rotors 121a and 121b shown in FIG. 5. The first rotor 121a includes a barrel 141a and a blade 143a provided on the barrel 141a. In a similar manner to the first rotor 121a, the second rotor 121b includes a barrel 141b and a blade 143b provided on the barrel 141b.

Diameters of these barrels 141a and 141b are relatively large. This is to prevent, during kneading or, more specifically, during shearing the rubber raw material and mixing the rubber raw material with the various materials by rotations of the rotors 121a and 121b, forces large enough to destroy the rotors 121a and 121b from acting thereon. Another reason is that cooling tubes are passed through the barrels 141a and 141b in order to absorb heat generated by kneading.

A gap between a tip of the blade 143a and an inner wall 145a of the kneading chamber 119a and a gap between a tip of the blade 143b and an inner wall 145b of the kneading chamber 119b are set small in order to increase efficiencies of shearing of the rubber raw material and dispersion of the various material in the rubber raw material.

As described above, the gaps are set small and, at the same time, diameters of the barrels 141a and 141b are set relatively large. Accordingly, since a blind spot θ1 is inevitably created when viewing the kneading chambers 119a and 119b or more specifically, for example, the inner wall 145a of the kneading chamber 119a from the kneaded article discharge port 133, an area that is not viewable exists on the inner wall 145a.

The first rotor 121a and the second rotor 121b configured as described above rotate around a rotary shaft 147 in the kneading chamber 119b due to a drive force of a motor (not shown).

Figure 2:
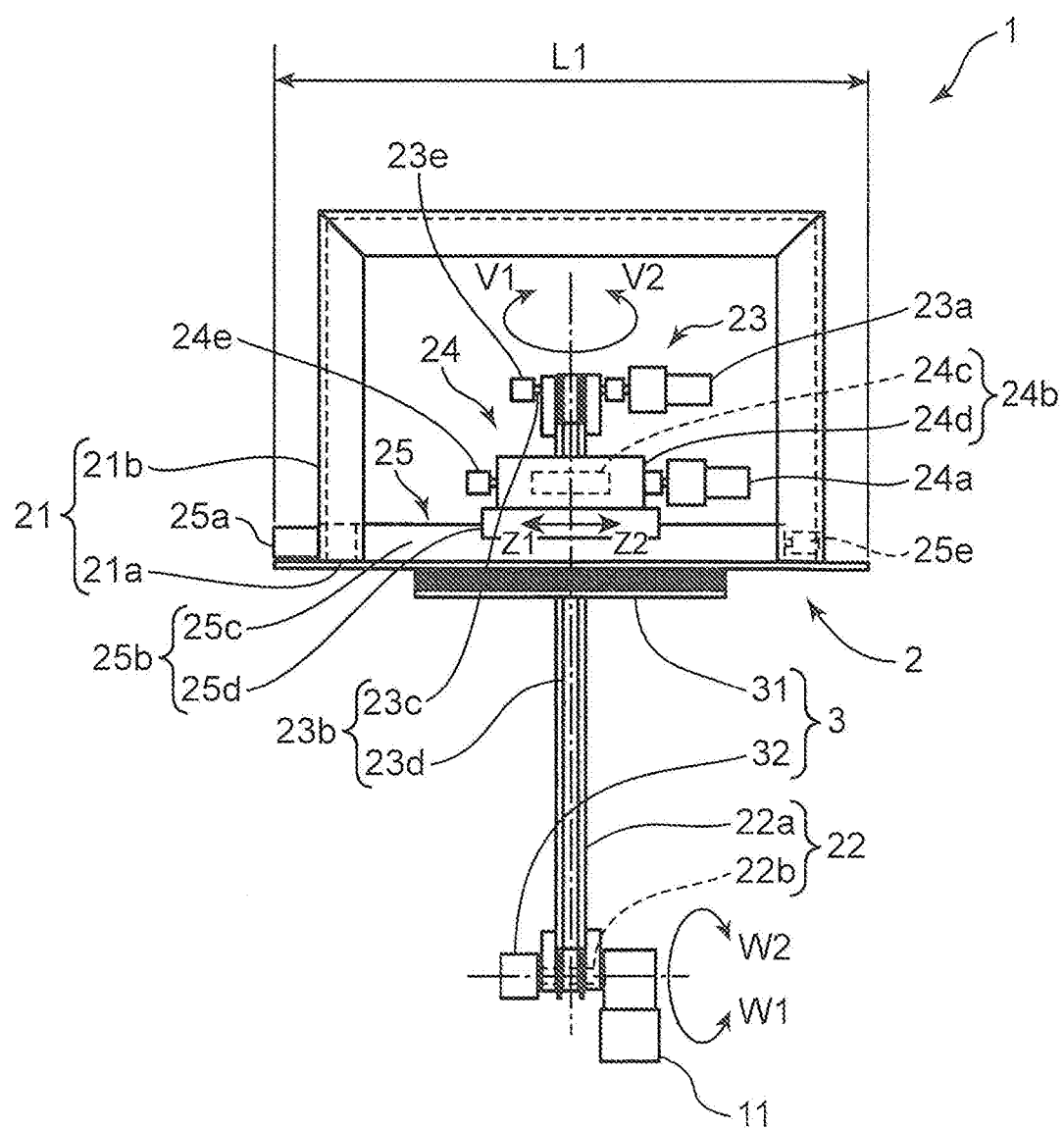
FIG. 2 is a front view of a photographing unit used in the kneader internal inspection device shown in FIG. 1.
Figure 3:
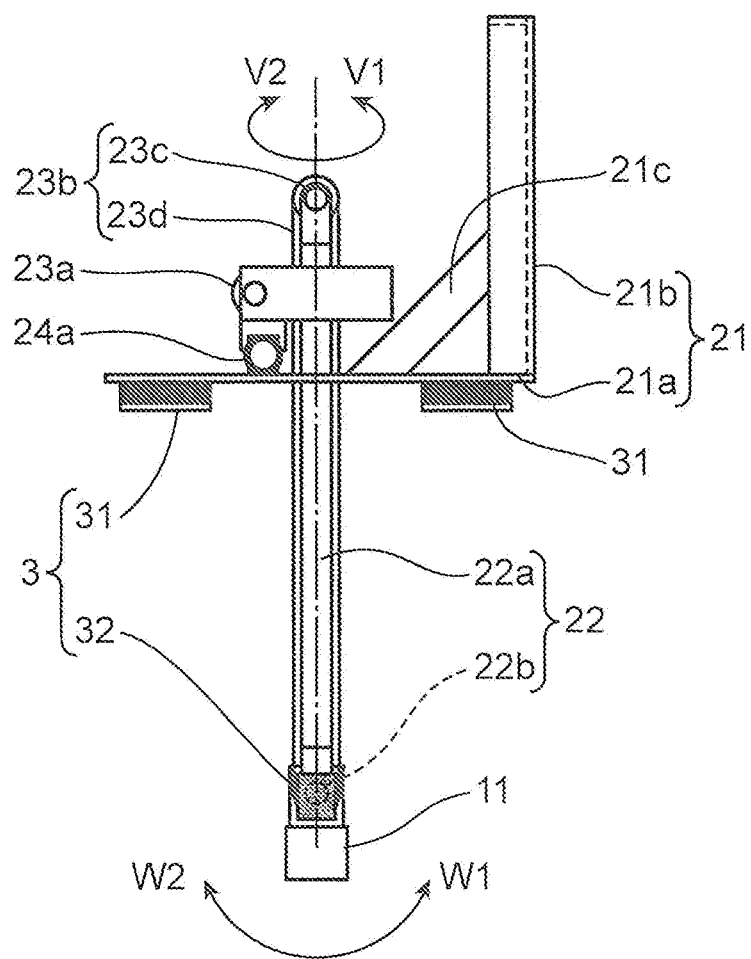
FIG. 3 is a side view of FIG. 2.
Figure 4:
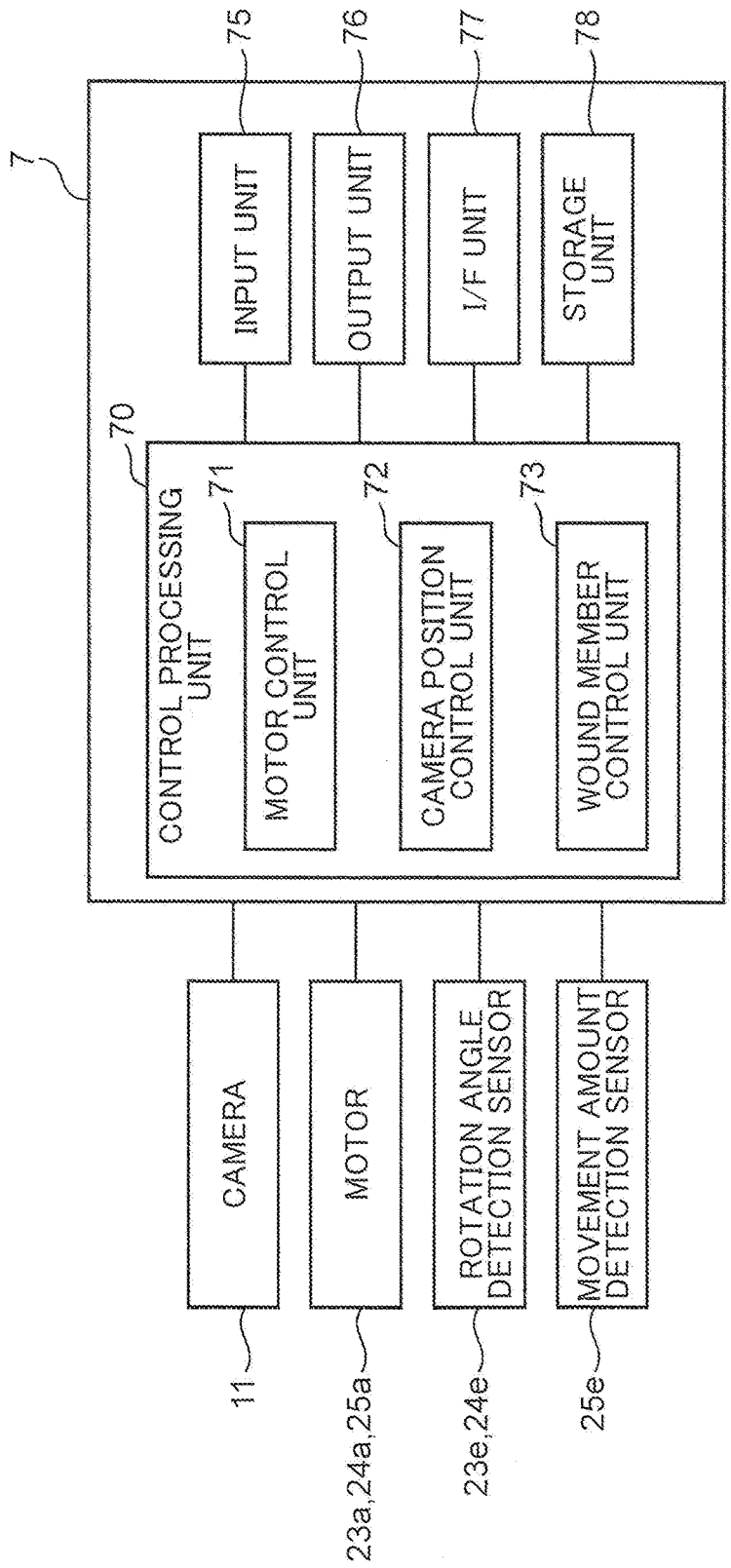
FIG. 4 is a block diagram showing a configuration of a computer used in the kneader internal inspection device shown in FIG. 1.

Next, the kneader internal inspection device 10 according to the present embodiment will be described. FIG. 1 is a schematic diagram of a state where an interior of a kneader is being inspected by a kneader internal inspection device according to an embodiment. FIG. 2 is a front view of a photographing unit used in the kneader internal inspection device shown in FIG. 1. FIG. 3 is a side view of FIG. 2. FIG. 4 is a block diagram showing a configuration of a computer used in the kneader internal inspection device shown in FIG. 1. For example, as shown in FIG. 1, the kneader internal inspection device 10 includes a photographing unit 1 which photographs the interior of the kneader 100, an illuminating unit 3 which illuminates the interior of the kneader 100, a suspending and supporting member 4 which suspends and supports the photographing unit 1 in the interior of the kneader 100, and an operating unit 5 for operating the photographing unit 1 from outside the kneader 100.

The photographing unit 1 includes a camera 11 which photographs a subject and which generates, for example, an image such as a still image or a moving image, and a camera holding member 2 which holds the camera 11.

As shown in FIG. 2 and FIG. 3, the camera holding member 2 includes a frame 21, a camera holding unit main body 22 which holds the camera 11, and camera movably operating units 23 to 25 which movably operate the camera 11.

The frame 21 includes a rectangular first frame 21a which is arranged horizontally and a rectangular second frame 21b which is coupled to the first frame 21a. A length L1 in a width direction of the first frame 21a is set smaller than widths of the material feed throat 111 and the hopper 127 so as to enable the first frame 21a to enter the material feed throat 111 through the hopper 127.

The length L1 in the width direction of the first frame 21a is more or less equal to a length L2 (shown in FIG. 7) in an axial direction of the first kneading chamber 119a and the second kneading chamber 119b formed inside the casing 117 or, in other words, a length L2 in a direction of a rotational axis D1 of the rotors 121a and 121b.

In the second frame 21b, a lower end thereof is fixedly coupled to a front end (one end) of the first frame 21a, and an upper end thereof extends upward from the front end of the first frame 21a. Accordingly, the first frame 21a and the second frame 21b are orthogonal to each and form an L-shape in a side view. Moreover, in the present embodiment, the first frame 21a and the second frame 21b are reinforced for the sake of preventing deformation thereof by a reinforcing member 21c having one end coupled to the first frame 21a and another end coupled to the second frame 21b.

The camera holding unit main body 22 includes an elongated holding body 22a with an elongated shape and a camera mounting shaft 22b on which the camera 11 is mounted.

A longitudinal direction of the elongated holding body 22a is aligned with the vertical direction, and the elongated holding body 22a is rotatably held by the first frame 21a around an axial center of the elongated holding body 22a or, in other words, around an vertical axis (V1-V2) in a state where a lower end of the elongated holding body 22a protrudes downward from the first frame 21a.

The camera mounting shaft 22b is rotatably mounted to the lower end of the elongated holding body 22a so as to extend in a horizontal direction and constitute a horizontal shaft (a shaft parallel to the rotary shaft 147 of the rotors 121a and 121b).

The camera movably operating unit includes a horizontal axis-centered rotating member 23 which rotates the camera 11 around the horizontal axis, a vertical axis-centered rotating member 24 which rotates the camera 11 around the vertical axis, and a moving member 25 which moves the camera 11 in a direction of the rotational axis of the rotors 121a and 121b.

The horizontal axis-centered rotating member 23 includes a first motor 23a which is mounted to the elongated holding body 22a and a first rotation transmitting member 23b which transmits rotation of the first motor 23a to the camera 11.

In the present embodiment, the first rotation transmitting member 23b includes a belt winding shaft 23c which is rotatably mounted to an upper end of the elongated holding body 22a and an endless belt 23d hung around the belt winding shaft 23c and the camera mounting shaft 22b.

The belt winding shaft 23c is coupled so as to be capable of transmitting rotation to the first motor 23a via a gear (not shown).

The endless belt 23d travels in accordance with a rotation of the belt winding shaft 23c and rotates the camera mounting shaft 22b. In accordance with the rotation of the camera mounting shaft 22b, the camera 11 rotates around the camera mounting shaft 22b or, in other words, around the horizontal axis (W1-W2).

In the present embodiment, the horizontal axis-centered rotating member 23 includes a rotation angle detection sensor 23e which detects a rotation angle of the camera 11 around the horizontal axis. The horizontal axis-centered rotation angle detection sensor 23e according to the present embodiment is mounted to the belt winding shaft 23c and detects a rotation angle of the camera 11 around the horizontal axis by detecting an amount of rotation of the belt winding shaft 23c.

The vertical axis-centered rotating member 24 includes a second motor 24a which is mounted to the first frame 21a and a second rotation transmitting member 24b which transmits rotation of the second motor 24a to the camera 11.

The second rotation transmitting member 24b includes a cylindrical worm gear 24c which is mounted to the elongated holding body 22a and a wheel 24d which meshes with the worm gear 24c.

The wheel 24d is mounted to the first frame 21a and, at the same time, coupled so as to be capable of transmitting rotation to the second motor 24a via a gear (not shown).

With the vertical axis-centered rotating member 24 configured as described above, the worm gear 24c rotates via the wheel 24d in accordance with an operation of the second motor 24a, and the elongated holding body 22a rotates together with the worm gear 24c around an axial center of the elongated holding body 22a or, in other words, around the vertical axis (V1-V2).

In the present embodiment, the vertical axis-centered rotating member 24 includes a vertical axis-centered rotation angle detection sensor 24e which detects a rotation angle of the camera 11 around the vertical axis. The vertical axis-centered rotation angle detection sensor 24e according to the present embodiment is mounted to the wheel 24d and detects a rotation angle of the camera 11 around the vertical axis by detecting an amount of rotation of the wheel 24d.

The moving member 25 includes a third motor 25a which is mounted to the first frame 21a and a third rotation transmitting member 25b which transmits rotation of the third motor 25a to the camera 11.

The third rotation transmitting member 25b includes a guide screw shaft 25c and a moving screw member 25d which is screwed to the guide screw shaft 25c.

The guide screw shaft 25c extends in the width direction of the first frame 21a and is rotatably mounted to the first frame 21a. The guide screw shaft 25c is coupled so as to be capable of transmitting rotation to the third motor 25a via a gear (not shown).

The moving screw member 25d is fixedly coupled to the elongated holding body 22a. Moreover, the third rotation transmitting member 25b is not limited to a configuration including the guide screw shaft 25c and the moving screw member 25d and may be modified as appropriate. For example, the third rotation transmitting member 25b may be configured so as to move the elongated holding body 22a, which holds the camera 11, in the width direction of the first frame 21a.

In the present embodiment, the moving member 25 includes a movement amount detection sensor 25e which detects a movement amount of the camera 11. The movement amount detection sensor 25e according to the present embodiment is mounted to the guide screw shaft 25c and detects a movement amount of the camera 11 by detecting an amount of rotation of the guide screw shaft 25c.

With the moving member 25 configured as described above, the guide screw shaft 25c rotates in accordance with an operation of the third motor 25a. The moving screw member 25d moves toward one side or the other side in the width direction of the first frame 21a along the guide screw shaft 25c in accordance with a rotation of the guide screw shaft 25c and, in accordance with the movement of the moving screw member 25d, the elongated holding body 22a moves together with the moving screw member 25d in a same direction (a Z1-Z2 direction). This movement makes the camera 11 movable in the direction of the rotational axis D1 of the first rotor 121a and the second rotor 121b.

Next, the illuminating unit 3 will be described. The illuminating unit 3 according to the present embodiment includes two types of illuminations, namely, an entire illumination (first illumination) 31 which illuminates an entire interior of the kneader 100 and a close-up illumination (second illumination) 32 which is smaller than the entire illumination 31 and which partially illuminates the interior of the kneader 100.

The entire illumination 31 is constituted by two units mounted on a lower surface of the first frame 21a on both sides of the elongated holding body 22a so as to sandwich the elongated holding body 22a. Each entire illumination 31 is configured to illuminate downward.

The close-up illumination 32 is fixedly mounted to the camera mounting shaft 22b in a state of facing a same direction as the camera 11. Therefore, the close-up illumination 32 is operated by the camera movably operating units 23 to 25 so as to rotate around the horizontal axis and the vertical axis and to move in the width direction of the first frame 21a together with the camera 11.

Next, the suspending and supporting member 4 will be described. The suspending and supporting member 4 according to the present embodiment includes, for example, a wire rope 41 and a signal cable 42 which communicably connects the photographing unit 1 and the operating unit 5 to each other as shown in FIG. 1.

One end of the wire rope 41 is coupled to an upper end of the second frame 21b in the frame 21 of the photographing unit 1. Another end of the wire rope 41 is coupled to a suspension operating unit of the operating unit 5 to be described later.

The wire rope 41 is configured so as to be guided by a wire rope guiding pulley 41a which is attached to the hopper openable lid 127a.

In the present embodiment, the signal cable 42 is constituted by a bundle of a plurality of signal cables which respectively communicably connect the camera 11, the motors 23a, 24a, and 25a, the horizontal axis-centered rotation angle detection sensor 23e, the vertical axis-centered rotation angle detection sensor 24e, and the movement amount detection sensor 25e with the operating unit 5.

Respective one ends of the signal cables 42 are coupled to the camera 11, the motors 23a, 24a, and 25a, and the like of the photographing unit 1 described above, and respective other ends of the signal cables 42 are coupled to the suspension operating unit 6 of the operating unit 5 to be described later.

The signal cable 42 is configured so as to be guided by a signal cable guiding pulley 42a which is attached to the hopper openable lid 127a.

Next, the operating unit 5 will be described. In the present embodiment, as shown in FIG. 1, the operating unit 5 includes the suspension operating unit 6 which operates the suspending and supporting member 4 and a computer (for example, a personal computer) 7.

The suspension operating unit 6 operates so as to sequentially wind up the wire rope 41 and the signal cable 42 of the suspending and supporting member 4 from other ends thereof and to sequentially unwind the wound wire rope 41 and the wound signal cable 42 of the suspending and supporting member 4 using a motor (not shown).

For example, as shown in FIG. 4, the personal computer 7 includes a control processing unit 70, an input unit 75, an output unit 76, an interface unit (I/F unit) 77, and a storage unit 78.

The control processing unit 70 controls respective units of the personal computer 7 in accordance with functions of the respective units. The control processing unit 70 is configured so as to include, for example, a CPU (central processing unit) and peripheral circuits thereof.

The control processing unit 70 according to the present embodiment includes a motor control unit 71, a camera position control unit 72, and a wound member control unit 73.

The motor control unit 71 respectively controls the first motor 23a, the second motor 24a, and the third motor 25a so as to start operation and respectively controls the first motor 23a, the second motor 24a, and the third motor 25a so as to stop operation.

The camera position control unit 72 controls a rotation angle of the camera 11 around the horizontal axis based on detection information of the horizontal axis-centered rotation angle detection sensor 23e. The camera position control unit 72 controls a rotation angle of the camera 11 around the vertical axis based on detection information of the vertical axis-centered rotation angle detection sensor 24e. The camera position control unit 72 controls a movement amount of the camera 11 in an axial direction of the rotors 121a and 121b based on detection information of the movement amount detection sensor 25e.

The wound member control unit 73 controls the suspension operating unit 6 so as to perform a winding operation of the suspending and supporting member 4 and to perform an unwinding operation of the wound suspending and supporting member 4.

The input unit 75 is a device which is connected to the control processing unit 70 and which is used to input, for example, various commands and various necessary data, and the like to the personal computer 7. For example, the input unit 75 is a plurality of input switches having been assigned prescribed functions, a keyboard, a mouse, or the like.

The output unit 76 is a device which is connected to the control processing unit 70 and which outputs commands and data input from the input unit 75 and image data captured by the camera 11 under control of the control processing unit 70. For example, the output unit 76 is a display apparatus such as a CRT display, an LCD, or an organic EL display, a printing apparatus such as a printer, and the like.

The I/F unit 77 is a circuit which is connected to the control processing unit 70 and which performs data input and output to and from external devices under control of the control processing unit 70. For example, the I/F unit 77 is an interface circuit compliant with RS-232C which is a serial communication system, an interface circuit using Bluetooth (registered trademark), an interface circuit which performs infrared communication based on the IrDA (Infrared Data Association) standard or the like, or an interface circuit using the USB (Universal Serial Bus) standard.

The I/F unit 77 according to the present embodiment communicates with, for example, the camera 11, the motors 23a, 24a, and 25a, the horizontal axis-centered rotation angle detection sensor 23e, the vertical axis-centered rotation angle detection sensor 24e, the movement amount detection sensor 25e, and the suspension operating unit 6 via the signal cable 42.

The storage unit 78 is a circuit which is connected to the control processing unit 70 and which stores various prescribed programs and various pieces of prescribed data under the control of the control processing unit 70. The storage unit 78 includes, for example, a ROM (read only memory) which is a non-volatile storage element or an EEPROM (electrically erasable programmable read only memory) which is a rewritable non-volatile storage element. In addition, the storage unit 78 includes a RAM (random access memory) to act as a so-called working memory of the control processing unit 70 which stores data and the like created during execution of the prescribed programs.

Figure 8:
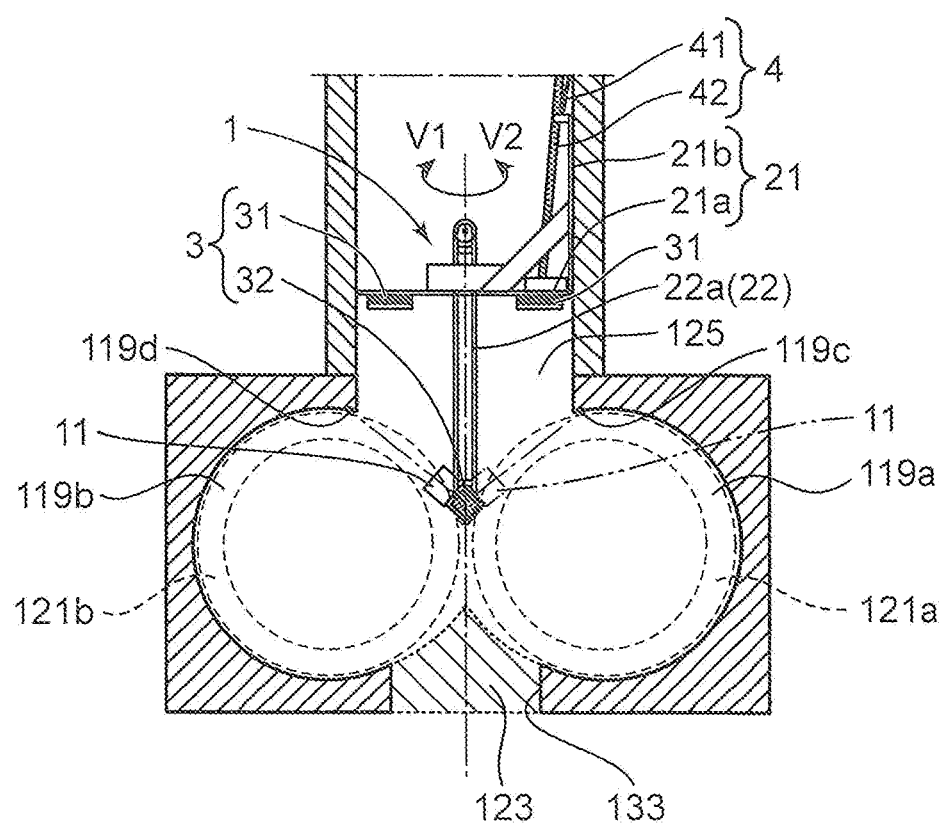
FIG. 8 is an explanatory diagram of an inspection of the interior of a kneader by a kneader internal inspection device.
Figure 9:
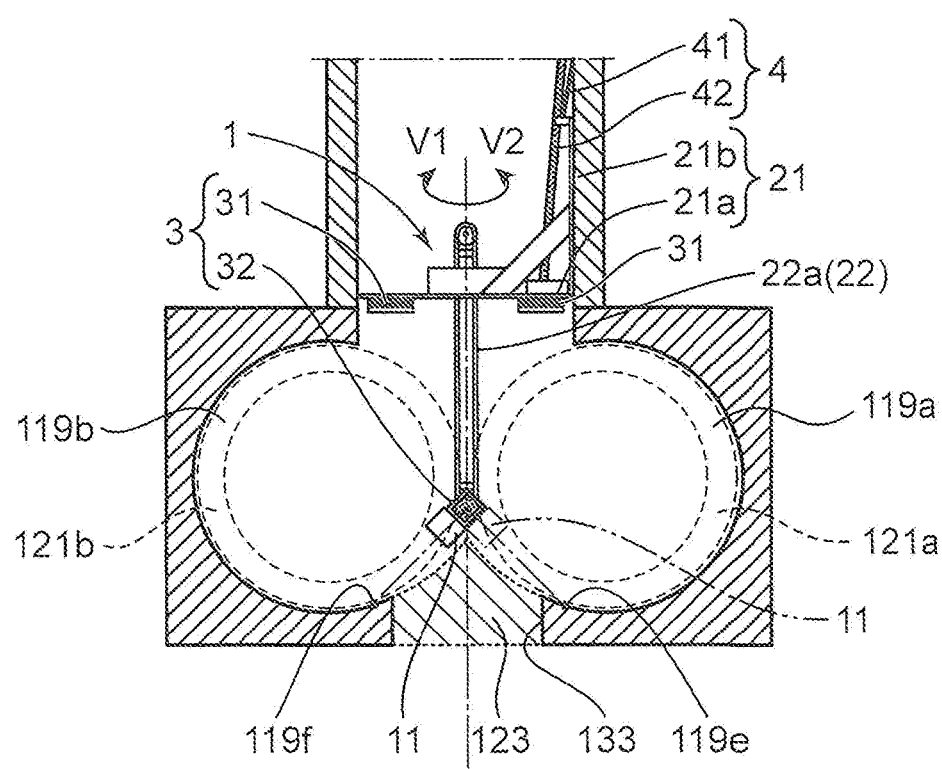
FIG. 9 is another explanatory diagram of an inspection of the interior of a kneader by a kneader internal inspection device.

Next, a method of inspecting the interior of the kneader 100 by the kneader internal inspection device 10 will be described. FIG. 8 is an explanatory diagram of an inspection of the interior of a kneader by a kneader internal inspection device. FIG. 9 is another explanatory diagram of an inspection of the interior of a kneader by a kneader internal inspection device.

As shown in FIG. 1, first, the photographing unit 1 of the kneader internal inspection device 10 is placed in the interior of the kneader 100 from the hopper 127. Next, by operating the personal computer 7, the suspension operating unit 6 is operated and the camera 11 of the photographing unit 1 is lowered to, for example, a position of the material supply port 125 of the kneader 100.

In addition, in this state, the operation of the suspension operating unit 6 is stopped. In this state, the second frame 21b of the photographing unit 1 conforms to an inner wall of the kneader 100, the second frame 21b is vertically arranged, and the first frame 21a is horizontally arranged.

From this state, by operating the personal computer 7, the first motor 23a is operated, the camera 11 is made to face the first rotor 121a from an obliquely upward side of the first rotor 121a, and the operation of the first motor 23a is stopped in this state. When necessary, the second motor 24a is operated by operating the personal computer 7 to rotate the camera 11 around the vertical axis.

From this state, by operating the personal computer 7, the third motor 25a is operated, and the first rotor 121a is slowly rotated while the camera 11 moves in the direction of the rotational axis D1 of the first rotor 121a (refer to FIG. 7). Accordingly, the camera 11 can photograph a state of the blade 143a of the first rotor 121a along the direction of the rotational axis of the first rotor 121a and, by referring to an image photographed by the camera 11, a user (operator) can observe the state of the blade 143a of the first rotor 121a along the direction of the rotational axis of the first rotor 121a.

In addition, by operating the personal computer 7, the first motor 23a is operated, the camera 11 is made to face the second rotor 121b from an obliquely upward side of the second rotor 121b, and the operation of the first motor 23a is stopped in this state. From this state, by operating the personal computer 7, the third motor 25a is operated, and the second rotor 121b is slowly rotated while the camera 11 moves in the direction of the rotational axis D1 of the second rotor 121b. Accordingly, the camera 11 can photograph a state of the blade 143b of the second rotor 121b along the direction of the rotational axis of the second rotor 121b and, by referring to an image photographed by the camera 11, the user (operator) can observe the state of the blade 143b of the second rotor 121b along the direction of the rotational axis of the second rotor 121b.

Next, for example, by operating the personal computer 7 as shown in FIG. 8, the suspension operating unit 6 is operated and the photographing unit 1 is lowered until the camera 11 reaches an approximately vertically central position of the kneading chambers 119a and 119b of the kneader 100.

In this state, the operation of the suspension operating unit 6 is stopped. By operating the personal computer 7, the first motor 23a is operated, the camera 11 is made to face obliquely upward a boundary 119c between an inner wall of the first kneading chamber 119a and the material supply port 125, and the operation of the first motor 23a is stopped in this state. In addition, when necessary, the second motor 24a is operated by operating the personal computer 7 to rotate the camera 11 around the vertical axis.

From this state, by operating the personal computer 7, the third motor 25a is operated and the camera 11 moves in the direction of the rotational axis D1 of the first rotor 121a. Accordingly, the camera 11 can photograph a state of the boundary 119c, which is susceptible to damage, between the inner wall of the first kneading chamber 119a and the material supply port 125 and, by referring to an image photographed by the camera 11, the user (operator) can observe the state of the boundary 119c along the direction of the rotational axis of the first rotor 121a. In doing so, although it is difficult for the entire illumination 31 to illuminate the boundary 119c between the inner wall of the first kneading chamber 119a and the material supply port 125, since the close-up illumination 32 constantly faces a same direction as the camera 11, the close-up illumination 32 can reliably illuminate the boundary 119c.

By operating the personal computer 7, the first motor 23a is operated, the camera 11 is made to face a boundary 119d between an inner wall of the second kneading chamber 119b and the material supply port 125, and the operation of the first motor 23a is stopped in this state. From this state, by operating the personal computer 7, the third motor 25a is operated and the camera 11 is moved in the direction of the rotational axis D1 of the second rotor 121b. Accordingly, the camera 11 can photograph a state of the boundary 119d, which is susceptible to damage, between the inner wall of the second kneading chamber 119b and the material supply port 125 and, by referring to an image photographed by the camera 11, the user (operator) can observe the state of the boundary 119d along the direction of the rotational axis of the second rotor 121b. In this case, similarly, the close-up illumination 32 can reliably illuminate the boundary 119d.

Next, for example, by operating the personal computer 7 as shown in FIG. 9, the suspension operating unit 6 is operated and the camera 11 of the photographing unit 1 is lowered until reaching a position that is approximately below the kneading chambers 119a and 119b of the kneader 100.

In this state, the operation of the suspension operating unit 6 is stopped. By operating the personal computer 7, the first motor 23a is operated, the camera 11 is made to face a boundary 119e between the inner wall of the first kneading chamber 119a and the kneaded article discharge port 133, and the operation of the first motor 23a is stopped in this state. In addition, when necessary, the second motor 24a is operated by operating the personal computer 7 to rotate the camera 11 around the vertical axis.

From this state, by operating the personal computer 7, the third motor 25a is operated and the camera 11 moves in the direction of the rotational axis D1 of the first rotor 121a. Accordingly, the camera 11 can photograph a state of the boundary 119e, which is susceptible to damage, between the inner wall of the first kneading chamber 119a and the kneaded article discharge port 133 and, by referring to an image photographed by the camera 11, the user (operator) can observe the state of the boundary 119e along the direction of the rotational axis of the first rotor 121a.

By operating the personal computer 7, the first motor 23a is operated, the camera 11 is made to face a boundary 119f between the inner wall of the second kneading chamber 119b and the kneaded article discharge port 133, and the operation of the first motor 23a is stopped in this state. From this state, by operating the personal computer 7, the third motor 25a is operated and the camera 11 moves in the direction of the rotational axis D1 of the second rotor 121b. Accordingly, the camera 11 can photograph a state of the boundary 119f, which is susceptible to damage, between the inner wall of the second kneading chamber 119b and the kneaded article discharge port 133 and, by referring to an image photographed by the camera 11, the user (operator) can observe the state of the boundary 119f along the direction of the rotational axis of the second rotor 121b.

As described above, since the kneader internal inspection device 10 suspends and supports the photographing unit 1 so as to be vertically movable in the interior of the kneader 100 with the suspending and supporting member 4, the interior of the kneader 100 from an upper part to a lower part thereof can be photographed by the photographing unit 1 and an inspection can be reliably performed without having to disassemble the kneader 100.

Since the camera holding member 2 holds the camera 11 in the interior of the kneader 100 so as to be rotatable around the vertical axis and the horizontal axis, an upper part, a lower part, a right part, and a left part of the inner wall in the interior of the kneader 100 as well as a an upper part, a lower part, a right part, and a left part of the rotors can be observed and the interior of the kneader 100 can be inspected in detail. For example, since the entire interior of the kneader 100 can be viewed with one camera 11, the kneader internal inspection device 10 can be simplified and manufactured at low cost, and can be made more user-friendly.

Since the camera holding member 2 holds the camera 11 in the interior of the kneader 100 so as to be movable in the axial direction of the rotors, the kneader internal inspection device 10 can observe inner walls and the rotors in the interior of the kneader 100 along the axial direction of the rotors. As a result, the interior of the kneader 100 can be inspected in greater detail.

Moreover, while the camera 11 is configured to include one camera in the embodiment described above, for example, the camera 11 may be configured to include a plurality of cameras arranged so as to face various directions and can be modified as appropriate.

In addition, while the camera holding member 2 holds the camera 11 so as to be immovable in a direction of an optical axis of the camera 11 in the embodiment described above, alternatively, the camera holding member 2 may hold the camera 11 so as to be movable in the direction of the optical axis (X1-X2 in FIG. 10) of the camera 11.

Figure 10A:
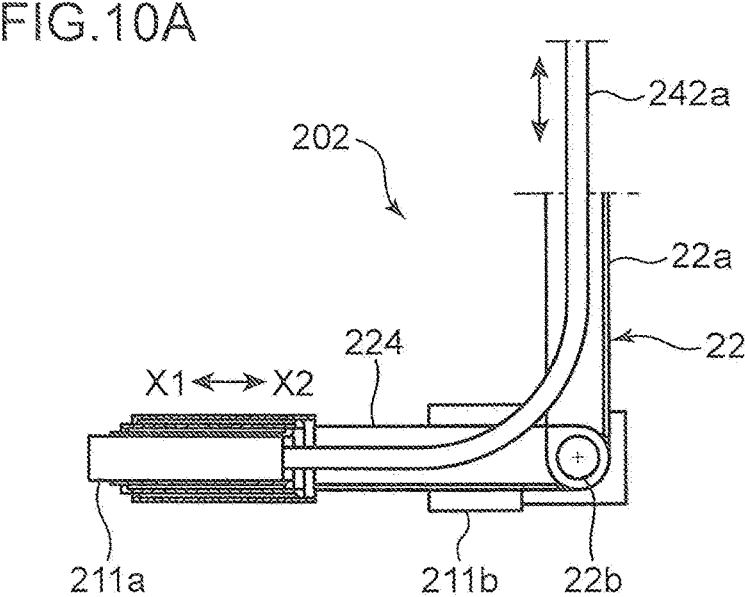
FIG. 10 is a diagram showing another embodiment of a camera holding member of the photographing unit used in the kneader internal inspection device shown in FIG. 1.
Figure 10B:
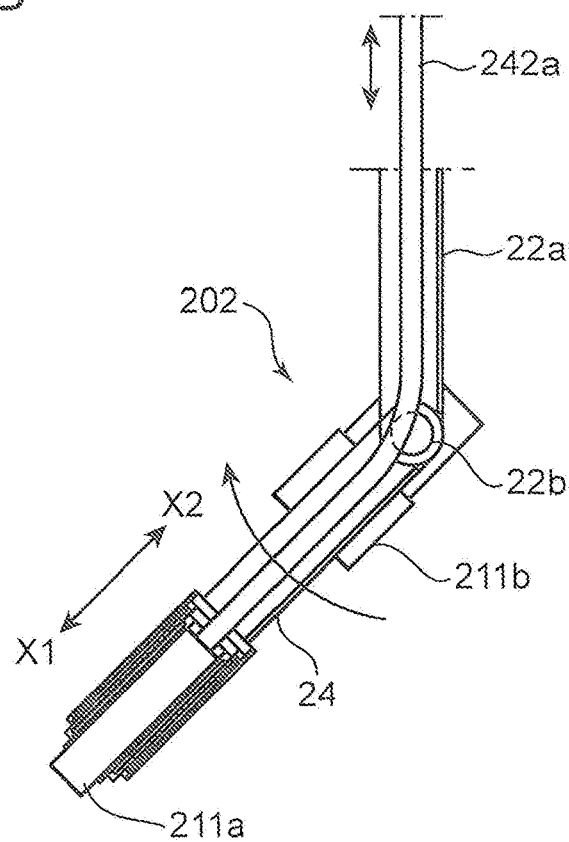
Figure 11A:
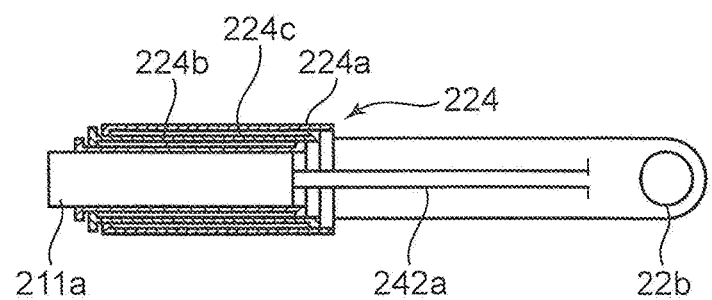
FIG. 11 is a partial enlarged view of the camera holding member shown in FIG. 10.
Figure 11B:
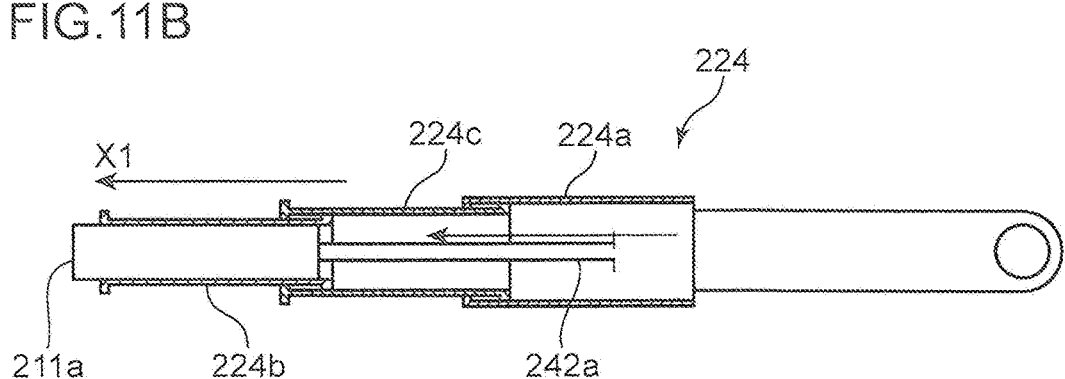

FIG. 10 is a diagram showing another embodiment of a camera holding member of the photographing unit used in the kneader internal inspection device shown in FIG. 1. FIG. 10A is a partial side view of another embodiment of the camera holding member used in the photographing unit, and FIG. 10B is a side view of a state where a camera optical axis direction moving unit included in the camera holding member has been rotated and operated from the state shown in FIG. 10A. FIG. 11 is a partial enlarged view of the camera holding member shown in FIG. 10. FIG. 11A is an enlarged sectional view of the camera optical axis direction moving unit of the camera holding member shown in FIG. 10, and FIG. 11B is an enlarged sectional view of a state where the camera optical axis direction moving unit of the camera holding member has been extended from the state shown in FIG. 11A.

Specifically, for example, as shown in FIG. 10A and FIG. 10B, a camera holding member 202 includes the camera holding unit main body 22 and an extensible camera optical axis direction moving unit 224 which is coupled to the camera holding unit main body 22. The camera holding unit main body 22 includes the elongated holding body 22a and the camera mounting shaft 22b in a similar manner to the embodiment described above.

As shown in FIG. 11, the camera optical axis direction moving unit 224 includes a first cylindrical body 224a having a cylindrical section, a second cylindrical body 224b which has a cylindrical shape and which holds a first camera 211a, and a third cylindrical body 224c which has a cylindrical shape and which is arranged between the first cylindrical body 224a and the second cylindrical body 224b.

One end of the first cylindrical body 224a is fixedly coupled to the camera mounting shaft 22b as shown in FIG. 10 and FIG. 11. The third cylindrical body 124c is slidably and non-rotatably fitted to and inserted into an inner circumference of the first cylindrical body 124a. The second cylindrical body 224b is slidably and non-rotatably fitted to and inserted into an inner circumference of the third cylindrical body 224c.

With the camera holding member 202 configured as described above, in a similar manner to the embodiment described above, the camera optical axis direction moving unit 224 rotates in accordance with a rotation of the camera mounting shaft 22b as shown in FIG. 10B and the first camera 211a rotates together with the camera optical axis direction moving unit 224. When a pushing operation of a signal cable 242 connected to the first camera 211a is performed, as shown in FIG. 11B, the third cylindrical body 224c slides in the first cylindrical body 224a, the second cylindrical body 224b slides in the third cylindrical body 224c and, accordingly, an overall length of the camera optical axis direction moving unit 224 increases. On the other hand, when a pulling operation (winding operation) of the signal cable 242 is performed, the third cylindrical body 224c and the second cylindrical body 224b respectively move in directions opposite to those described above and, accordingly, the overall length of the camera optical axis direction moving unit 224 decreases and is restored to an original length.

By adopting the configuration described above, the first camera 211a can be brought closer to a side of an object to be inspected and a point of interest can be observed in greater detail.

Moreover, the camera optical axis direction moving unit 224 is not limited to a mode constituted by three cylindrical bodies including the first to third cylindrical bodies 224a to 224c and may be modified as appropriate as long as the second cylindrical body 224b which slides relative to the first cylindrical body 224a is included. The camera optical axis direction moving unit 224 may be constituted by two cylindrical bodies or four or more cylindrical bodies.

In addition, the camera optical axis direction moving unit is not limited to modes constituted by two or more cylindrical bodies and may be modified as appropriate. For example, a camera optical axis direction moving unit 324 may be constituted by an extensible diamond lattice structure as shown in FIG. 12. FIG. 12 is a diagram showing yet another embodiment of a camera holding member of the photographing unit used in the kneader internal inspection device shown in FIG. 1. FIG. 12A is a partial side view of yet another embodiment of the camera holding member, and FIG. 12B is a side view of a state where a camera optical axis direction moving unit included in the camera holding member has been extended from the state shown in FIG. 12A.

Specifically, in the camera optical axis direction moving unit 324, a plurality of link pieces 325a in which the link pieces 325a are axially supported against each other by pins 326 are consecutively assembled in a lattice-like manner. One end in a longitudinal direction of the camera optical axis direction moving unit 324 is fixedly coupled to the camera mounting shaft 22b, and another end in the longitudinal direction of the camera optical axis direction moving unit 324 fixedly holds a first camera 311a.

With the camera optical axis direction moving unit 324 configured as described above, as ends 325b of two link pieces 325a which are axially supported against each other by the pins 326 are subjected to a pressing operation in a direction in which the ends 325b approach each other by a pressing member (not shown), an overall length of the camera optical axis direction moving unit 324 increases as shown in FIG. 12B. On the other hand, when a pulling operation (winding operation) of a signal cable 342 connected to the first camera 311a is performed, a force is applied in a direction in which the ends of the link pieces 325a described above separate from each other and, accordingly, the overall length of the camera optical axis direction moving unit 324 decreases and is restored to an original length shown in FIG. 12A.

In addition, while only the first camera 211a or 311a may be provided in cases where the camera optical axis direction moving unit 224 or 324 as shown in FIG. 10 or FIG. 12 is provided, a second camera 211b or 311b which is mounted to the camera mounting shaft 22b so as to be immovable in the camera optical axis direction may be provided in addition to the first camera 211a or 311a as respectively shown in FIG. 10 and FIG. 12A.

Furthermore, for example, when a point of interest is discovered on an object by an inspection using the second camera 211b or 311b, an observation in greater detail may be performed by bringing the first camera 211a or 311a close to the point of interest.

Figure 13:
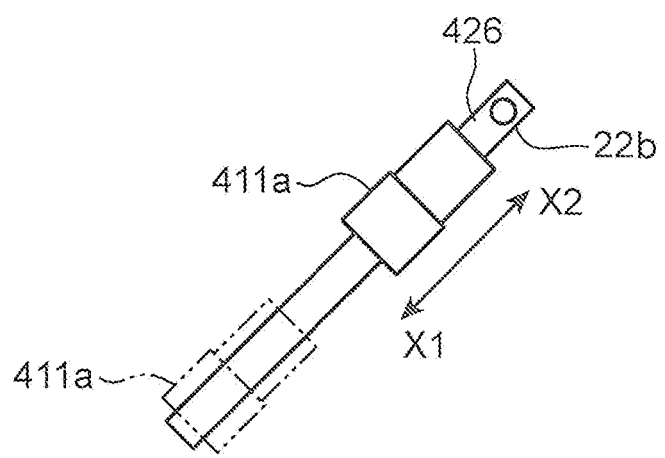
FIG. 13 is a partial side view of another embodiment of the camera holding member.

The camera optical axis direction moving unit is not limited to modes in which an overall length is extended or contracted and may be modified as appropriate. For example, as shown in FIG. 13, a guide shaft 426 of which one end is mounted to the camera mounting shaft 22b may be provided, in which case the camera optical axis direction moving unit may be configured so as to be movable along an optical axis direction (X1-X2 direction) of a first camera 411a as the first camera 411a slides along an axial direction of the guide shaft 426. However, in this case, when the first camera 411a has not been brought close to an object, since a state is created where the guide shaft 426 protrudes toward a tip side from the first camera 411a, there is a risk that the guide shaft 426 may interfere with the rotors 121a and 121b during a rotation operation in the kneading chambers 119a and 119b or that, for example, the guide shaft 426 may hinder photography by the first camera 411a. Therefore, in this case, the extensible camera optical axis direction moving unit shown in FIG. 10 or FIG. 12 which does not create such risks is favorably provided.

While the present description discloses techniques of various modes as presented above, major techniques thereof may be summarized as follows.

A kneader internal inspection device according to an aspect includes: a photographing unit which is arranged in an interior of a kneader and which photographs the interior; an illuminating unit which illuminates the interior of the kneader; a suspending and supporting member which suspends and supports in the interior of the kneader the photographing unit so as to be vertically movable; and an operating unit which operates the photographing unit from outside the kneader.

With such a kneader internal inspection device, an internal state of a kneader becomes readily observable with a small number of people and a preliminary examination can be performed before inspecting respective units in the interior of the kneader by disassembling and opening the kneader. Therefore, appropriate maintenance can be performed. For example, if wear and tear inside the kneader is minimal, maintenance can be conducted by rationally determining necessary intervals such as extending maintenance intervals without performing a full-scale inspection of the respective units in the interior of the kneader which involves disassembling and opening the kneader. Since downtime of the kneader is shorter and there are fewer operational constraints, an inspection plan can be more readily formulated, an inspection can be performed with less manpower, and an advantage can also be gained in terms of cost required for the inspection.

In the kneader internal inspection device described above, since the photographing unit is suspended and supported so as to be vertically movable in the interior of the kneader with the suspending and supporting member, the kneader internal inspection device is capable of photographing the interior of the kneader from an upper part to a lower part thereof with the photographing unit without, for instance, having to disassemble the kneader, and an inspection can be reliably performed and an inspection of the interior of the kneader can be easily performed.

According to another aspect, in the kneader internal inspection device described above, the photographing unit includes a camera and a camera holding member which holds the camera, and the camera holding member holds the camera so as to be rotatable around a horizontal axis and rotatable around a vertical axis.

In such a kneader internal inspection device, an inner wall of a casing in the interior of the kneader can be observed from an upper part to a lower part of the inner wall or a rotor provided in the interior of the kneader can be observed from an upper part to a lower part of the rotor via the camera and the interior of the kneader can be inspected in detail. For example, since approximately an entire interior of the kneader can be viewed with one camera, the kneader internal inspection device can be simplified and manufactured at low cost, and can be made more user-friendly.

According to another aspect, in the kneader internal inspection devices described above, the photographing unit includes a camera and a camera holding member which holds the camera, and the camera holding member holds the camera so as to be movable in a direction of the horizontal axis.

In such a kneader internal inspection device, an inner wall of a casing in the interior of the kneader and a rotor provided in the interior of the kneader can be observed along an axial direction of the rotor via the camera and the interior of the kneader can be inspected in greater detail. For example, since approximately an entire interior of the kneader can be viewed with one camera, the kneader internal inspection device can be simplified and manufactured at low cost, and can be made more user-friendly.

According to another aspect, in the kneader internal inspection devices described above, the photographing unit and the operating unit are configured so as to be capable of transmitting and receiving electric signals to and from each other via a signal cable, and the suspending and supporting member is the signal cable. In other words, the photographing unit and the operating unit are connected to each other via a signal cable for transmitting and receiving electric signals, and the photographing unit is suspended and supported so as to be vertically movable in the interior of the kneader by the signal cable.

In such a kneader internal inspection device, since a signal cable suspends and supports the photographing unit, a separate suspending and supporting member such as a wire rope for suspending and supporting the photographing unit is no longer necessary and the kneader internal inspection device can be simplified and made more user-friendly.

According to another aspect, in the kneader internal inspection devices described above, the photographing unit and the operating unit are configured so as to be capable of transmitting and receiving electric signals to and from each other in a wireless manner, and the suspending and supporting member includes a wire rope extended to the outside from the interior of the kneader.

In such a kneader internal inspection device, since a signal cable for sending electric signals between the photographing unit and the operating unit is no longer necessary, the kneader internal inspection device can be simplified and made more user-friendly.

According to another aspect, in the kneader internal inspection devices described above, the camera holding member includes a camera holding member main body and a camera optical axis direction moving unit which is coupled to the camera holding member main body, and the camera optical axis direction moving unit holds the camera so as to be movable along a direction of an optical axis of the camera.

In such a kneader internal inspection device, since a camera can be brought close to a side of an object to be inspected, for example, a point of interest discovered by an observation can be observed in greater detail.

According to another aspect, in the kneader internal inspection device described above, the camera optical axis direction moving unit includes a first cylindrical body which is coupled to the camera holding member main body and a second cylindrical body which holds the camera, and the second cylindrical body is coupled to the first cylindrical body so as to be slidable in an axial direction thereof.

In such a kneader internal inspection device, an entire length extends or contracts as the second cylindrical body slides in the axial direction of the first cylindrical body and the camera can be brought closer to a side of an object to be inspected. When there is no need to bring the camera close to the object, by contracting the entire kneader internal inspection device, the entire camera optical axis direction moving unit becomes compact and more easily arrangeable in the interior of the kneader, and the camera optical axis direction moving unit can be prevented from hindering photography by the camera.

According to another aspect, in the kneader internal inspection device described above, the camera optical axis direction moving unit is an extensible diamond lattice structure in which a plurality of link pieces that are axially supported against each other are consecutively assembled in a lattice-like manner, the camera holding member main body is coupled to one end of the structure, and the camera is held by another end of the structure.

In such a kneader internal inspection device, a length of the entire structure extends or contracts by applying a force in a direction perpendicular to a length direction to a part of the diamond lattice structure, and the camera can be brought closer to a side of an object to be inspected. When there is no need to bring the camera close to the object, by contracting the entire kneader internal inspection device, the entire camera optical axis direction moving unit becomes compact and more easily arrangeable in the interior of the kneader, and the camera optical axis direction moving unit can be prevented from hindering photography by the camera.

The present application claims priority on the basis of Japanese Patent Application No. 2014-163711 filed on Aug. 11, 2014, the entire contents of which are incorporated herein by reference.

Although the present invention has been described above in an appropriate and sufficient manner in the form of embodiments with reference to the drawings, those skilled in the art will understand that various modifications and/or improvements may be readily made to the embodiments described above. Therefore, it is to be understood that all modifications and/or improvements implemented by those skilled in the art shall fall within the scope of the claims presented below unless such modifications and/or improvements constitute departures from the scope of the claims.

INDUSTRIAL APPLICABILITY

According to the present invention, a kneader internal inspection device can be provided.

The invention claimed is:

1. A kneader internal inspection device, comprising:
a photographing unit which is arranged in an interior of a kneader and which photographs the interior, the photographing unit including a camera and a holding member which holds the camera, the holding member including a frame, an elongated holding body rotatably held by the frame around an axial center of the elongated holding body, and a mounting shaft rotatably mounted to a lower end of the elongated holding body;
an illuminating unit directly mounted on a lower surface of the frame to illuminate the interior of the kneader;
a suspending and supporting member which suspends and supports, in the interior of the kneader, the frame so as to be vertically movable; and
an operating unit which operates the photographing unit from outside the kneader.

2. The kneader internal inspection device according to claim 1, wherein
the holding member holds the camera so as to be rotatable around a horizontal axis and rotatable around a vertical axis.

3. The kneader internal inspection device according to claim 1, wherein
the holding member holds the camera so as to be movable in a direction of the horizontal axis.

4. The kneader internal inspection device according to claim 1, wherein
the photographing unit and the operating unit are configured so as to be capable of transmitting and receiving electric signals to and from each other via a signal cable, and
the suspending and supporting member is the signal cable.

5. The kneader internal inspection device according to claim 1, wherein
the photographing unit and the operating unit are configured so as to be capable of transmitting and receiving electric signals to and from each other in a wireless manner, and
the suspending and supporting member includes a wire rope extended to the outside from the interior of the kneader.

6. The kneader internal inspection device according to claim 1, wherein
the holding member includes a holding member main body and an optical axis direction moving unit which is coupled to the holding member main body, and
the optical axis direction moving unit holds the photographing unit so as to be movable along a direction of an optical axis of the photographing unit.

7. The kneader internal inspection device according to claim 6, wherein
the optical axis direction moving unit includes a first cylindrical body which is coupled to the holding member main body and a second cylindrical body which holds the photographing unit, and
the second cylindrical body is coupled to the first cylindrical body so as to be slidable in an axial direction thereof.

8. The kneader internal inspection device according to claim 6, wherein
the optical axis direction moving unit is an extensible diamond lattice structure in which a plurality of link pieces that are axially supported against each other are consecutively assembled in a lattice-like manner,
the holding member main body is coupled to one end of the structure, and
the photographing unit is held by another end of the structure.

* * * * *